US008465424B2

(12) United States Patent
Aggarwal

(10) Patent No.: US 8,465,424 B2
(45) Date of Patent: Jun. 18, 2013

(54) MOBILE DEVICE AND SYSTEM FOR MONITORING AND RECORDING BODY VITAL SIGNS

(75) Inventor: Sudhir Aggarwal, Fremont, CA (US)

(73) Assignee: Sudhir Aggarwal, Fremont, CA (US)

( * ) Notice: Subject to any disclaimer, the term of this patent is extended or adjusted under 35 U.S.C. 154(b) by 801 days.

(21) Appl. No.: 12/053,765

(22) Filed: Mar. 24, 2008

(65) Prior Publication Data
US 2009/0240118 A1    Sep. 24, 2009

(51) Int. Cl.
*A61B 5/00* (2006.01)
*A61B 5/02* (2006.01)

(52) U.S. Cl.
USPC ........... 600/300; 600/301; 600/485; 600/490; 600/499

(58) Field of Classification Search
None
See application file for complete search history.

(56) References Cited

U.S. PATENT DOCUMENTS

| | | | | |
|---|---|---|---|---|
| 5,243,992 A | * | 9/1993 | Eckerle et al. ................ | 600/503 |
| 5,490,505 A | * | 2/1996 | Diab et al. .................... | 600/323 |
| 5,908,027 A | * | 6/1999 | Butterfield et al. ........... | 600/485 |
| 5,941,828 A | * | 8/1999 | Archibald et al. ............ | 600/494 |
| 6,290,650 B1 | * | 9/2001 | Butterfield et al. ........... | 600/485 |
| 6,443,906 B1 | * | 9/2002 | Ting et al. ..................... | 600/490 |
| 6,558,335 B1 | * | 5/2003 | Thede ........................... | 600/503 |
| 6,616,613 B1 | * | 9/2003 | Goodman ...................... | 600/504 |
| 6,730,038 B2 | * | 5/2004 | Gallant et al. ................ | 600/485 |
| 6,746,400 B2 | * | 6/2004 | Rathjen ......................... | 600/405 |
| 6,918,879 B2 | * | 7/2005 | Ting et al. ..................... | 600/485 |
| 2006/0009697 A1 | * | 1/2006 | Banet et al. ................... | 600/485 |
| 2006/0079792 A1 | * | 4/2006 | Finburgh et al. .............. | 600/485 |
| 2007/0265533 A1 | | 11/2007 | Tran | |

* cited by examiner

*Primary Examiner* — Bill Thomson
*Assistant Examiner* — Shirley Jian
(74) *Attorney, Agent, or Firm* — Blakely, Sokoloff, Taylor & Zafman LLP

(57) ABSTRACT

A method and apparatus is disclosed herein for monitoring vital signs using a health monitor embedded into a mobile device. In one embodiment, the apparatus comprises a mobile device having an embedded health monitor to take measurements of vital signs of an individual, to determine vital sign parameters from the measurements, and to transfer the vital sign parameters; and a computing system communicably coupled to the mobile device to store the vital sign parameters and to perform trend analysis on stored vital sign parameters and to provide feedback to the user or user specified persons and generate alarms.

21 Claims, 8 Drawing Sheets

MOBILE DEVICE AND SYSTEM FOR MONITORING AND RECORDING BODY VITAL SIGNS

FIELD OF THE INVENTION

The present invention is related to the field of measuring and recording the body vital signs such as heart rate, blood pressure and temperature for health monitoring applications. More specifically, the present invention is related to mobile monitoring of body vital parameters and recording them to make them accessible any time/anywhere.

BACKGROUND OF THE INVENTION

As wireless connectivity technology is becoming more pervasive, there is a move to implement a wireless-based health monitoring system as described in patent application US patent application publication no. 2007/0265533. The wireless system described therein is very costly as it is based on very special devices for monitoring.

For body wellness monitoring, the most important parameters are the temperature, heart rate, blood pressure and the respiratory rate. These parameters are also known as body vital signs. Measurement of these parameters are generally simple with the exception of the blood pressure measurement which is the most difficult of all. For measuring blood pressure, there are many methods such as Auscultatory, Oscillometry, applanation tonometry, plethesmograpghy, etc. Most of the existing blood pressure monitors use either Auscultatory or oscillometric method for measuring the blood pressure. These methods require a cuff to be worn on arm which is inflated during measurement. Use of a cuff and the apparatus required for inflation make the measurement device power consuming and bulky and, as such, it cannot be carried easily in a pocket.

SUMMARY OF THE INVENTION

A method and apparatus is disclosed herein for monitoring vital signs using a health monitor embedded into a mobile device. In one embodiment, the apparatus comprises a mobile device having an embedded health monitor to take measurements of vital signs of an individual, to determine vital sign parameters from the measurements, and to transfer the vital sign parameters; and a computing system communicably coupled to the mobile device to store the vital sign parameters and to perform trend analysis on stored vital sign parameters.

BRIEF DESCRIPTION OF THE DRAWINGS

The present invention will be understood more fully from the detailed description given below and from the accompanying drawings of various embodiments of the invention, which, however, should not be taken to limit the invention to the specific embodiments, but are for explanation and understanding only.

DETAILED DESCRIPTION OF THE PRESENT INVENTION

Very compact and very low power blood pressure measurement techniques are described that can be easily embedded in mobile devices. A health awareness system that make use of such embedded mobile devices and the internet to provide feedback to the user any time, any where is also disclosed.

In the following description, numerous details are set forth to provide a more thorough explanation of the present invention. It will be apparent, however, to one skilled in the art, that the present invention may be practised without these specific details. In other instances, well-known structures and devices are shown in block diagram form, rather than in detail, in order to avoid obscuring the present invention.

A system having a mobile device and network access is disclosed. In one embodiment, the network access is via the internet. In one embodiment, the system is a health awareness system that facilitates monitoring of the body vitals any time and anywhere and offers the benefits of keeping a running record. In one embodiment, the system generates alerts and alarms if it detects that any of the body vital sign values are outside the normal limits. In one embodiment, the system generates messages (e.g., email or SMS messages) containing such information to be sent to the doctor, the user, and/or any such person chosen by the user.

Figure 1:
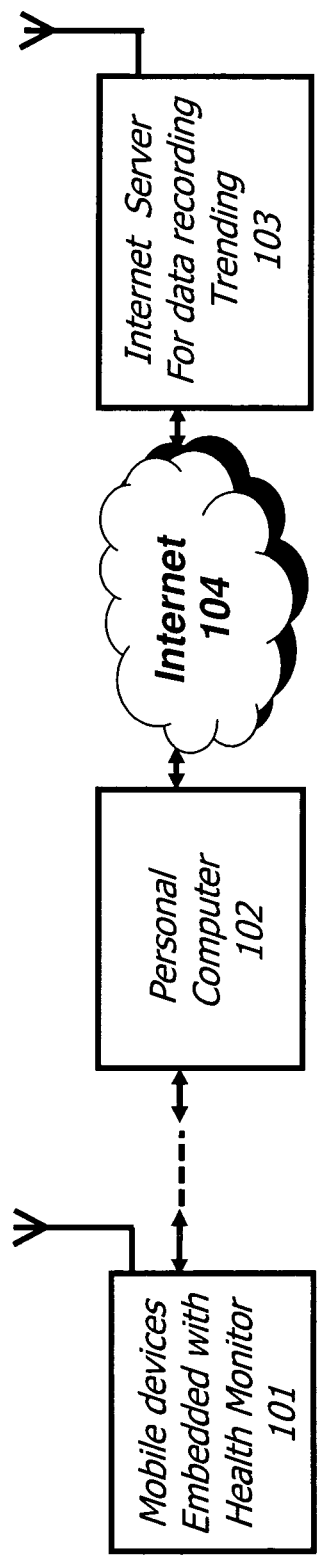
FIG. 1 shows the diagram of the proposed system for implementing a mobile health monitoring system with data recording and trending access any time any where.

FIG. 1 is a block diagram of a mobile health monitoring system with data recording and trending access. Referring to FIG. 1, a mobile device 101 has an embedded health monitor device and is communicably coupled with personal computer 102. Mobile device 101 may be a cellular phone, a portable media player (e.g., Ipod), a memory drive (e.g., USB flash memory thumb drive), a watch (e.g., a sports watch), a game controller, a laptop or other compact computer (e.g., a blackberry), a personal navigation device, a personal radio, a personal digital assistant, a pedometer, a stand-alone health monitor itself, etc. The embedded health monitor device measures the body vital signs and the data is stored, first, in a built-in memory of mobile device 101. Thereafter, in one embodiment, mobile device 101 transfers this data to a personal computer either by wireless (e.g., GSM, CDMA, WLAN, Bluetooth, Zigbee, UWB, etc.) or wired connectivity (e.g., USB, Ethernet, etc.) in a manner well known in the art. Personal computer 102 uploads the data transferred from mobile device 101 to server 103 via the Internet 104. In one embodiment, mobile device 101 communicates directly with server 103. Such mobile devices (e.g., cell phones) can access the Internet directly. Server 103 records the data transferred from mobile device 101 and performs trend and other analysis on the data. Examples of other analysis include computing the ratios and statistical estimates. Also in combination with other body parameters such as height and weight, the body mass index (BMI) can be computed to get good idea of health conditions, risk to heart disease etc. The data on server 103 can be accessed any time from any where with a user login and password. Based on the analysis of the data, in one embodiment, server 103 generates alert and alarms if the value of any of the vital signs is outside the normal limits. In such a case, server 103 generates messages (e.g., email messages, SMS messages, etc.) that are sent to user specified addresses.

Thus, as shown in FIG. 1, the system comprises a mobile device having an embedded health monitor to take measurements of the body of an individual, to determine vital signs of the body of the individual from the measurements, and to transfer the vital signs parameter values; and a computing system communicably coupled to the mobile device to store the vital signs values and to perform trend analysis on the vital parameters. The body vital sign parameters are computed from the measurement waveform by a micro-controller of a sensor device in the mobile device. These computed values are then transferred. In one embodiment, the measurement waveform (e.g., the waveform of FIG. 5) is also transmitted to the computing system or internet to extract more information from those. Although the system is described here for the body vital signs, it can be easily extended for other body parameters such as glucose, body fat, oxygen level, EKG signal, etc., by using appropriate sensors.

In one embodiment, the embedded health monitor device is very compact and consumes very low power. In one embodiment, in order to implement a very compact monitor, the monitor device uses a technique for blood pressure measurement that does not require cuff for inflation. The method is based on radial pulse tonometry. In one embodiment, the embedded health monitor has no moving parts to perform radial pulse tonometry. In one embodiment, the embedded health monitor performs radial pulse tonometry and generates an induced signal in resonance with pressure in an artery of the body from which one of the vital parameters is being measured without partial occlusion of the artery. In one embodiment, the embedded health monitor is operable to produce a voltage proportional to instantaneous blood pressure in the artery and create a waveform, the embedded health monitor obtaining systolic and diastolic blood pressure and heart rate of the body from the waveform. In one embodiment, the embedded health monitor includes a temperature sensor to measure temperature of the body.

Figure 2:
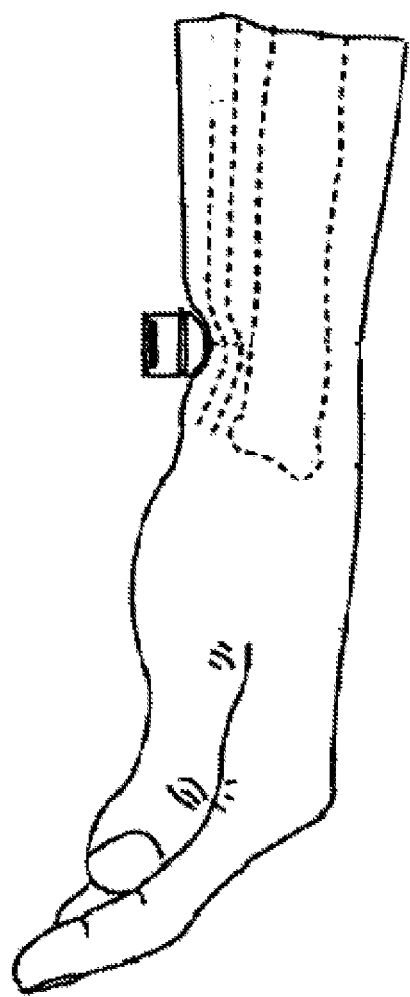
FIG. 2 illustrates use of the complex mechanical sensor for blood pressure measurement as per an applanation tonometry method.

In contrast, as described in U.S. Pat. No. 6,918,879, the tonometry applanation requires a prior art sensor to be placed on the skin over an artery underneath. The sensor is pressed on the artery that results in partial occlusion of the artery as shown in FIG. 2. In such a case, the physical movement of the surface due to blood pressure is picked-up by direct contact of the sensor. The very small mechanical movement is transferred through sophisticated housing to the electrical sensor as described in U.S. Pat. No. 6,918,879. The sensor used for such purpose are categorised as force or tactile pressure sensors, which are very costly because of complex mechanical sensitive parts.

Figure 3:
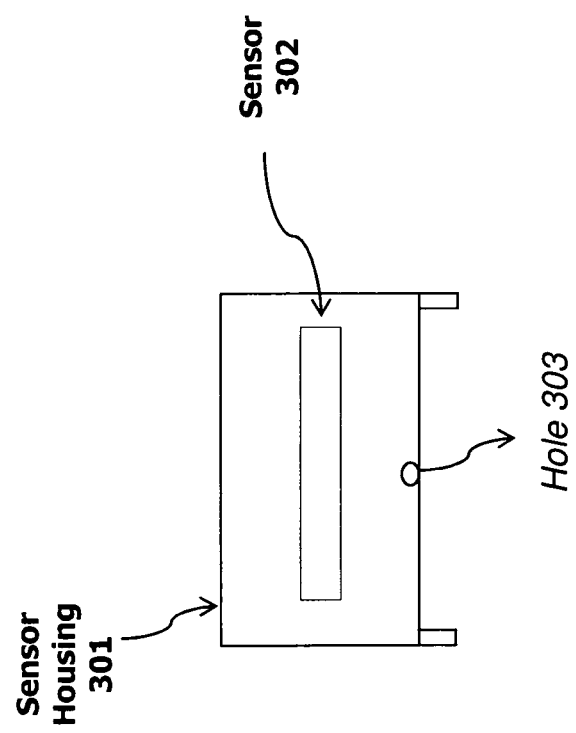
FIG. 3 illustrates a pressure sensor with a resonant cavity for use in one embodiment for the blood pressure measurement.

The method disclosed herein for performing a blood pressure measurement does not require partial occlusion of the artery. In the method described herein, the sensor is enclosed in a cavity that is placed on the skin over the artery. One embodiment of a simple pressure sensor is shown in FIG. 3. Referring to FIG. 3, pressure sensor 300 comprises a sensor housing 301, piezo-resistive sensor 302 and a hole 303 in the housing. The pressure from outside is transferred via hole 303 to the internal piezo-electric sensor. Piezo-resistive sensor 302 converts the pressure into an electrical signal. In one embodiment, pressure sensor 300 has no moving parts in it.

Figure 4:
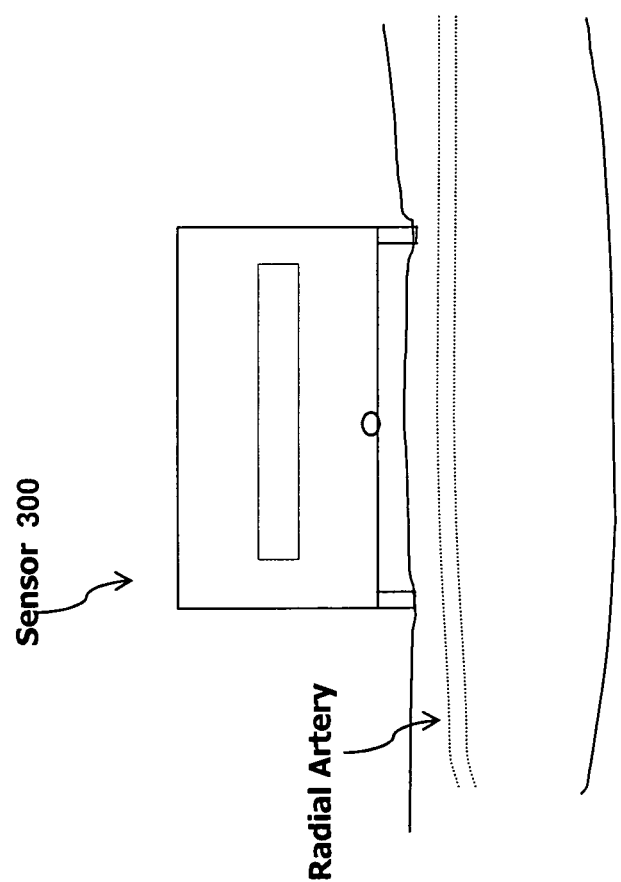
FIG. 4 illustrates the placement of the sensor over the radial artery on an arm.

Pressure sensor 300 may be placed on the wrist skin over the radial artery and the pulse pressure is transferred to electrical sensor 302 by use of cavity resonance as shown in FIG. 4. The cavity shape can be circular, rectangular or any shape. Although particular cavity shape is not a requirement, in one embodiment of the invention, a pressure sensor mounted in a square cavity is placed on the skin over the artery. The sensor housing is shown in FIG. 4. The pressure sensor in a cavity, as in FIG. 4, are easy to manufacture and are very cheap as there are no sensitive mechanical parts are involved.

Figure 5:
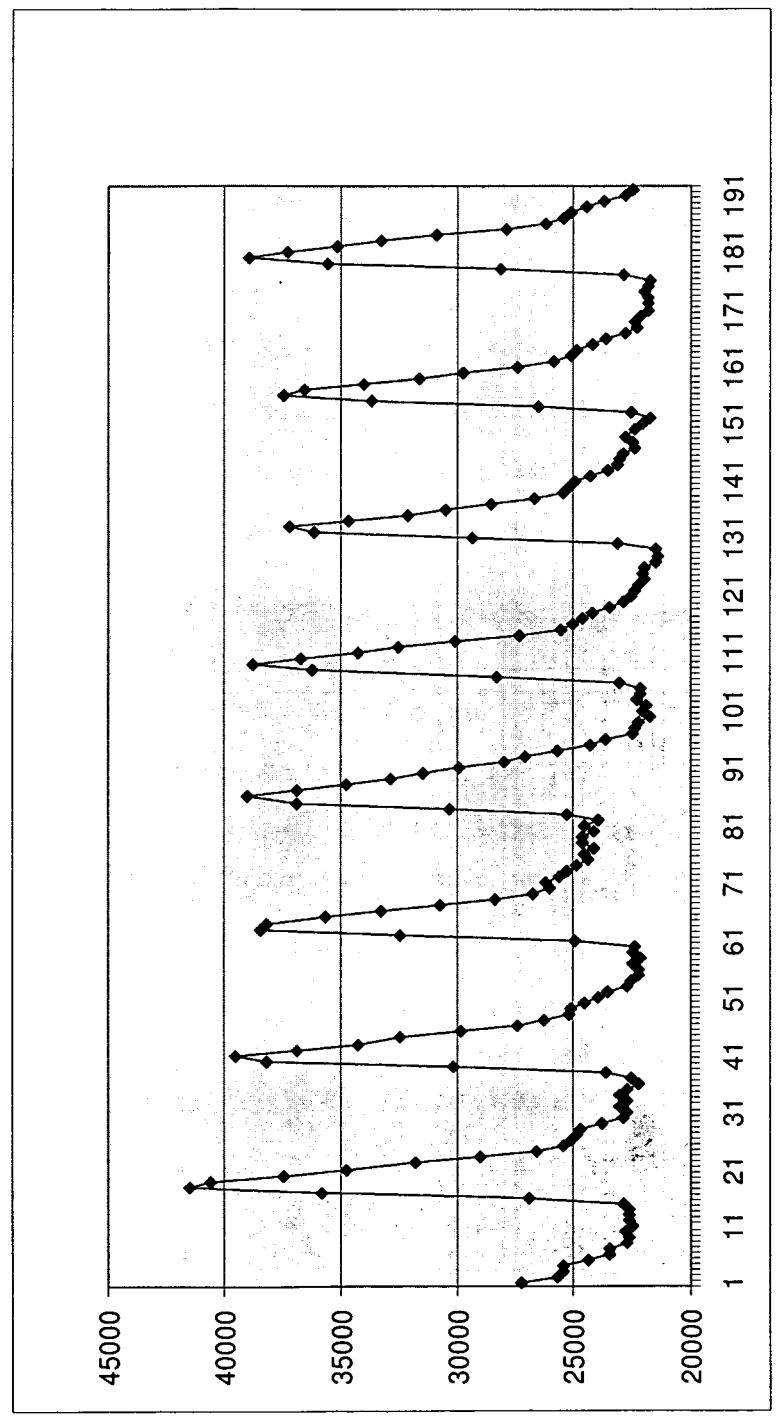
FIG. 5 shows a measure of a pressure waveform (in arbitrary units) as obtained by the sensor for further analysis to extract systolic and diastolic pressure.

In one embodiment, when sensor is placed on the artery as shown in FIG. 4, the induced pressure signal is in resonance with the artery blood pressure, and a voltage is produced by the pressure sensor that is proportional to the instantaneous blood pressure in the artery. Pressure sensor 300 captures a waveform corresponding to the instantaneous blood pressure. FIG. 5 is a plot of the measured pressure waveform. From such a waveform, the embedded health monitor device obtains the systolic and diastolic blood pressure of the individual, as well as the heart rate.

Figure 6:
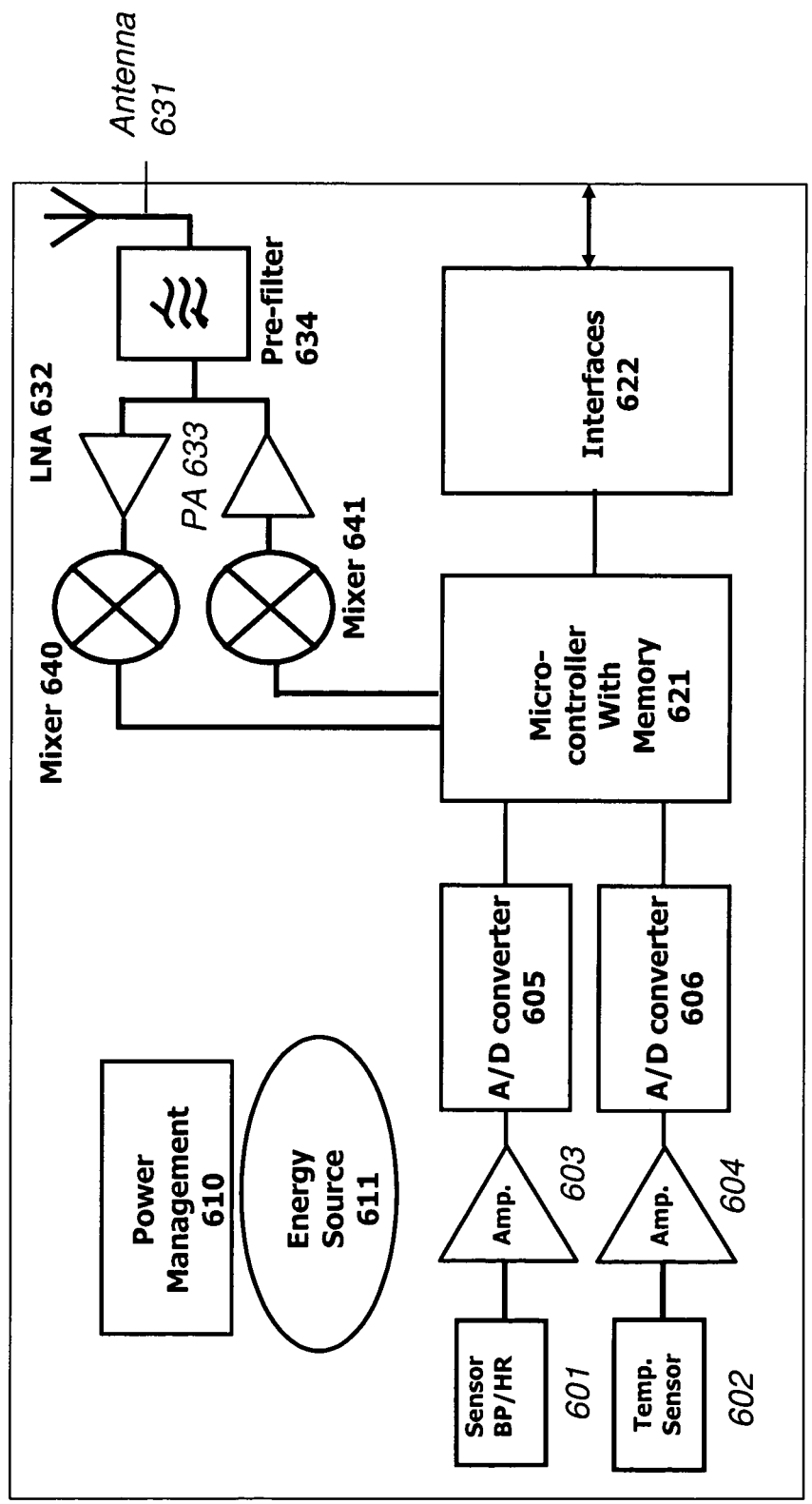
FIG. 6 is a block system diagram of a mobile sensor monitor for the blood pressure, heart rate and temperature body vital signs.

FIG. 6 is a block diagram of one embodiment of an embedded health monitor system. Referring to FIG. 6, a blood pressure/heart rate sensor 601 takes measurements from the body of an individual. The data corresponding to the measurements is amplified by amplifier 603 and then converted into digital format by analog-to-digital (A/D) converter 605. The digitized data is sent to microcontroller 621. Similarly, a temperature sensor 602 takes measurements of body temperature of the individual. The data corresponding to the measurements is amplified by amplifier 604 and then converted into digital format by analog-to-digital (A/D) converter 606. The digitized data is sent to microcontroller 621. Microcontroller 621 includes a memory to store the data received from sensors 601 and 602.

Microcontroller 621 processes the sensor data. In one embodiment, microcontroller 621 generates the waveform from sensor data from sensor 601 and from the waveform determines the blood pressure and heart rate information. Microcontroller 621 provides the data for local viewing on displays via interfaces 622 and for external transfer via wireless transmission. In one embodiment, interfaces 622 are also provided for wired connection of the device through a USB port, Ethernet port, or other well known serial or parallel port.

To communicate wirelessly, the embedded health monitor system includes antenna 631, low noise amplifier (LNA) 632, power amplifier (PA) 633, and mixers 640 and 641. Antenna 631 is coupled via pre-filter 634 to an input of a LNA 632 and an output of a PA 633. An input of mixer 640 is coupled to an output of LNA 632, and an output of mixer 640 is coupled to microcontroller 621. An input of mixer 641 is coupled to an output of microcontroller 621, while its output is coupled to an input of PA 633. Prefilter 634 is used to band limit the transmitted or received signal to the desired band.

The embedded health monitor system also includes an energy source 611 (e.g., a battery or locally generated) and a power management unit 610 that performs power management of different voltage supplies and regulation for the system.

In operation, as the amplitude of the sensor voltage from sensor 601 is small, amplifier 603 amplifies it. The amplified output voltage is given to A/D converter 605 where it is further amplified and converted to digital format. Each voltage is stored and over a period of time a voltage waveform is created and stored for further analysis by microcontroller 621 as explained above.

In one embodiment, the amount of time for which the waveform needs to be captured for analysis is dependent on the heart rate. In order to capture the slowest heart rate of about 40 beats per minute, at least 6 seconds of a waveform needs to be acquired, preferably, so that at least three peaks are captured.

The acquired waveform is analysed for the maximum and minimum values, also knows as peaks and valleys, respectively. The peaks of the waveform correspond to the systolic blood pressure. From the minimum value of the waveform immediately preceding the systolic peak, diastolic blood pressure is computed. In order to obtain an accurate estimate of maximum and minimum values, microcontroller 621 computes the average value of at least three corresponding peaks and three valleys. Microcontroller 621 determines the heart rate by examining the time interval between the peak values. Here again, microcontroller 621 computes a few time intervals between peaks. From these time intervals, microcontroller 621 calculates the heart rate. If the computed values of the heart rate from consecutive time intervals are different, then microcontroller 621 detects a condition of arrhythmia. Alternatively, these computations can be performed in the computer to which the data waveform is transferred instead of microcontroller 621 itself.

For measuring the temperature, temperature sensor 602 is placed close to pressure sensor 601. Both sensors operate in parallel, although the generated signals are handled separately as shown in FIG. 6. In one embodiment, this sensor system described herein is extended to measure one or more other body parameters such as, for example, but not limited to, body fat, glucose, oxygen level, and EKG signal in a similar manner by putting additional sensors in parallel paths. Thus, these sensors operate in parallel.

The methods described herein can be used for continuous measurement of beat-to-beat blood pressure as the complete blood pressure waveform is captured and is suitable for application in ambulatory blood pressure monitors also.

Trending of the data is done in a computer system (e.g., computer system 102, server 103, etc.) or by a computing device coupled to the internet where the measured data is transmitted for cumulative storage. In one embodiment, the data is analyzed and graphs are generated for the accumulated data. The accumulated data can be stored for years or any amount of time. In addition to the graphical feedback, in one embodiment, the system generates alerts/alarm to the user if the data values are outside normal limits or the trends are not normal. The system also generates messages (e.g., email messages, SMS messages, etc.) to send alerts/alarm to an individual (e.g., a doctor) or any such persons whose addresses are specified by the user.

Figure 7:
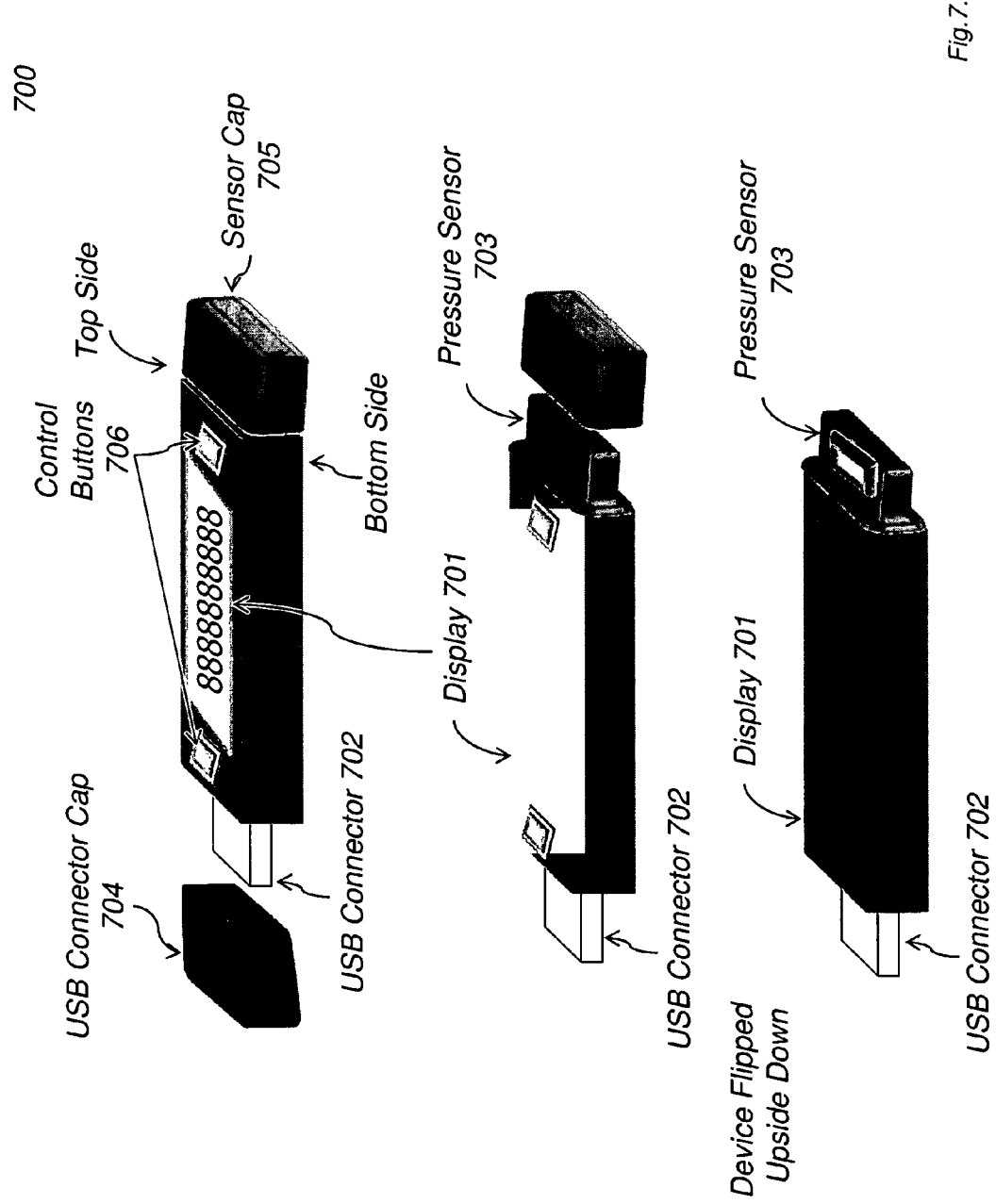
FIG. 7 illustrates one embodiment of a hardware implementation of a stand-alone compact health monitor with a display and a USB interface.

FIG. 7 is a block diagram of one embodiment of a standalone compact mobile health monitor. Referring to FIG. 7, health monitor 700 includes a display 701. Health monitor 700 also includes is a USB connector 702 as an interface on one end, while the other end has a pressure sensor 703 with rectangular cavity as described above. A USB connector cap 704 covers USB connector 702 and is removable to enable use of USB connector 702. In one embodiment, sensor 703 is located on the side opposite to the display side. This facilitates easy reading of the values from display 701 on top side, while pressure sensor 703 on the bottom side is placed on the radial artery. A sensor cap 705 covers pressure sensor 703 and is removable to enable use of pressure sensor 705. Control buttons 706 are located on the top side of health monitor 700 to control use of health monitor 700. The standalone device as described herein can be used as such or its functionality can be embedded in any of the mobile devices.

Figure 8:
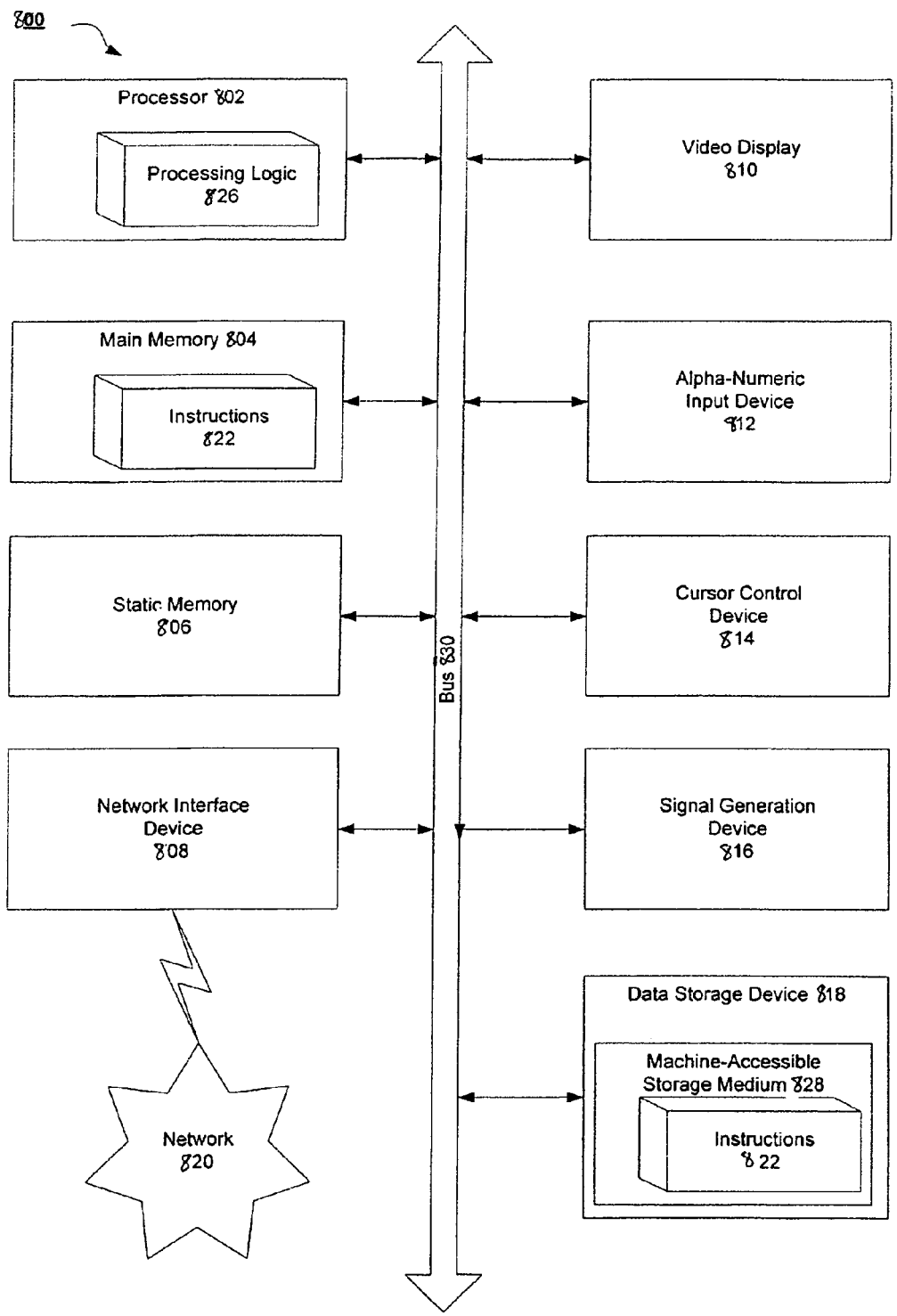
FIG. 8 is a block diagram of one embodiment of a computer system.

FIG. 8 illustrates a diagrammatic representation of a machine in the exemplary form of a computer system 800 within which a set of instructions, for causing the machine to perform any one or more of the methodologies discussed herein, may be executed. In alternative embodiments, the machine may be connected (e.g., networked) to other machines in a LAN, an internet, an extranet, or the Internet. The machine may operate in the capacity of a server or a client machine in a client-server network environment, or as a peer machine in a peer-to-peer (or distributed) network environment. The machine may be a personal computer (PC), a tablet PC, a set-top box (STB), a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The exemplary computer system 800 includes a processing device 802, a main memory 804 (e.g., read-only memory (ROM), flash memory, dynamic random access memory (DRAM) (such as synchronous DRAM (SDRAM) or Rambus DRAM (RDRAM), etc.), a static memory 806 (e.g., flash memory, static random access memory (SRAM), etc.), and a data storage device 818, which communicate with each other via a bus 830.

Processing device 802 represents one or more general-purpose processing devices such as a microprocessor, central processing unit, or the like. More particularly, the processing device may be complex instruction set computing (CISC) microprocessor, reduced instruction set computer (RISC) microprocessor, very long instruction word (VLIW) microprocessor, or processor implementing other instruction sets, or processors implementing a combination of instruction sets. Processing device 802 may also be one or more special-purpose processing devices such as an application specific integrated circuit (ASIC), a field programmable gate array (FPGA), a digital signal processor (DSP), network processor, or the like. The processing device 802 is configured to execute the processing logic 826 for performing the operations and steps discussed herein.

The computer system 800 may further include a network interface device 808. The computer system 800 also may include a video display unit 810 (e.g., a liquid crystal display (LCD) or a cathode ray tube (CRT)), an alphanumeric input device 812 (e.g., a keyboard), a cursor control device 814 (e.g., a mouse), and a signal generation device 816 (e.g., a speaker).

The data storage device 818 may include a machine-accessible storage medium 828 on which is stored one or more set of instructions (e.g., software 822) embodying any one or more of the methodologies of functions described herein. The software 822 may also reside, completely or at least partially, within the main memory 804 and/or within the processing device 802 during execution thereof by the computer system 800; the main memory 804 and the processing device 802 also constituting machine-accessible storage media. The software 822 may further be transmitted or received over a network 820 via the network interface device 808. In one embodiment, the network interface device 808 may be operable to receive messages from the broadcaster or the recipient as described above in various embodiments of the invention.

The machine-readable storage medium 828 may be used to store logic 8 of the health monitoring system, and/or a software library containing methods that call the above applications of embodiments of the invention. While the machine-accessible storage medium 828 is shown in an exemplary embodiment to be a single medium, the term "machine-accessible storage medium" should be taken to include a single medium or multiple media (e.g., a centralized or distributed database, and/or associated caches and servers) that store the one or more sets of instructions. The term "machine-accessible storage medium" shall also be taken to include any medium that is capable of storing, encoding or carrying a set of instruction for execution by the machine and that cause the machine to perform any one or more of the methodologies of the present invention. The term "machine-accessible storage medium" shall accordingly be taken to include, but not be limited to, solid-state memories, and optical and magnetic media.

In the above description, numerous specific details such as logic implementations, opcodes, resource partitioning, resource sharing, and resource duplication implementations, types and interrelationships of system components, and logic partitioning/integration choices may be set forth in order to provide a more thorough understanding of various embodiments of the invention. It will be appreciated, however, to one skilled in the art that the embodiments of the invention may be practiced without such specific details, based on the disclosure provided. In other instances, control structures, gate level circuits and full software instruction sequences have not been shown in detail in order not to obscure the invention. Those of ordinary skill in the art, with the included descriptions, will be able to implement appropriate functionality without undue experimentation.

Whereas many alterations and modifications of the present invention will no doubt become apparent to a person of ordinary skill in the art after having read the foregoing description, it is to be understood that any particular embodiment shown and described by way of illustration is in no way intended to be considered limiting. Therefore, references to details of various embodiments are not intended to limit the scope of the claims which in themselves recite only those features regarded as essential to the invention.

The invention claimed is:

1. An apparatus comprising:
a mobile device having an embedded health monitor adapted to take measurements of vital signs of an individual, determine blood pressure and heart rate parameters from the measurements, and transfer the parameters, wherein the embedded health monitor is adapted to perform radial pulse tonometry with a sensor enclosed in a sensor housing with an open cavity adapted to separate the sensor from skin over an artery when placed on a user, the open cavity adapted to become a closed cavity when placed on a user and utilize cavity resonance that transfers changing arterial pressure from the skin to the sensor through air moving in and out of a hole in a wall of the closed cavity, and pressure changes from the changing arterial pressure are transformed by the sensor to a pressure signal proportional to the pressure in the radial artery, and wherein the embedded health monitor is adapted to store the parameters in a memory of the mobile device and displays the stored parameters in a display of the mobile device; and
a remote computing system communicably coupled to the mobile device that is adapted to receive and store the parameters, transferred from the mobile device, and perform trend analysis on stored vital sign parameters.

2. The system defined in claim 1 wherein the embedded health monitor is adapted to generate an induced pressure signal from cavity resonance caused by an artery blood pressure of the body from which one of the measurements is being measured while preserving a normal throughput of the artery.

3. The system defined in claim 2 wherein the embedded health monitor is adapted to produce a voltage proportional to instantaneous blood pressure in the artery and create a waveform with the sensor, wherein the sensor is a piezo-resistive sensor, and wherein the embedded health monitor obtains systolic and diastolic blood pressure and heart rate of the body from the waveform.

4. The system defined in claim 1 wherein the embedded health monitor includes a temperature sensor adapted to measure temperature of the body.

5. The system defined in claim 1 wherein the embedded health monitor has no mechanical moving parts within the cavity.

6. The system defined in claim 1 wherein the embedded health monitor comprise a wireless transmitter adapted to communicate with a computing device via wireless communication.

7. The system defined in claim 1 wherein the mobile device comprises one of a group consisting of a cell phone, a portable media player, a memory device, a watch, a game controller, a laptop or other compact computer, a personal navigation device, a personal radio, a personal digital assistant, and a pedometer.

8. A system comprising:
a mobile device having an embedded health monitor device having
a blood pressure sensor and a temperature sensor that take blood pressure and temperature measurements, respectively, of a body of an individual, the blood pressure sensor having a sensor enclosed in a sensor housing with an open cavity adapted to separate the sensor from skin over an artery when placed on an individual, the open cavity adapted to become a closed cavity when placed on the individual and utilize cavity resonance that transfers changing arterial pressure from the skin to the sensor through air moving in and out of a hole in a wall of the closed cavity, and pressure changes from the changing arterial pressure are transformed by the sensor to a pressure signal proportional to the pressure in the radial artery of the individual to a waveform,
a pair of amplifiers coupled to the sensors that amplifies the sensed signal measurements,
a controller coupled to the pair of amplifiers that receives amplified signal measurement values and determines vital sign parameters from the amplified measurement values, and
a communication mechanism coupled to the controller that transfers the vital sign parameters; and
a remote computing system communicably coupled to the mobile device that receives and stores the vital sign parameters from the communication mechanism and performs trend analysis on one or more stored vital sign parameters generated from measurements to determine systolic and diastolic blood pressure and heart rate of the body.

9. The system defined in claim 8 wherein the blood pressure sensor performs radial pulse tonometry.

10. The system defined in claim 9 wherein the blood pressure sensor performs radial pulse tonometry and generates an induced pressure signal from an artery of the body from which one of the measurements is being measured.

11. The system defined in claim 10 wherein the blood pressure sensor produces a voltage proportional to instantaneous blood pressure in the artery and the controller creates a waveform using a piezo-resistive sensor, and wherein the embedded health monitor obtains the systolic and diastolic blood pressure and the heart rate of the body from the waveform.

12. The system defined in claim 8 wherein the blood pressure sensor has no mechanical moving parts within the cavity.

13. The system defined in claim 8 wherein the mobile device comprises one of a group consisting of a cell phone, a portable media player, a memory device, a watch, a game controller, a laptop or other compact computer, a personal navigation device, a personal radio, a personal digital assistant, and a pedometer.

14. The system defined in claim 8 wherein the embedded health monitor device comprises a USB port.

15. The system defined in claim 8 wherein the communication mechanism transfers the vital sign parameters from the mobile device to the computing system for analysis via a networked environment.

16. The system defined in claim 15 wherein the networked environment comprises the internet.

17. The system defined in claim 15 wherein the computing system accumulates the vital sign parameters over a period of time via the networked environment and generates alerts if analysis of the vital sign parameters indicates the vital sign parameters are outside a vital sign parameter limit.

18. The system defined in claim 17 wherein the analysis comprises generating graphs and trend analysis over a period of time.

19. A mobile device comprising:
an embedded health monitor device having
a blood pressure sensor and a temperature sensor that takes blood pressure and temperature measurements, respectively, of a body of an individual, the blood pressure sensor having a sensor enclosed in a sensor housing with an open cavity adapted to separate the sensor from skin over an artery when placed on an individual, the open cavity adapted to become a closed cavity when placed on the individual and utilize cavity resonance that transfers changing arterial pressure from the skin to the sensor through air moving in and out of a hole a wall of the closed cavity, and pressure changes from the changing arterial pressure are transformed by the sensor to a pressure proportional to pressure in a radial artery of the individual to a waveform,
a pair of amplifiers coupled to the sensors that amplify the measurements,
a controller coupled to the pair of amplifiers that receive amplified measurement values and determine vital sign parameters from the amplified measurement values, and
a communication mechanism coupled to the controller that transfers the vital sign parameters.

20. The mobile device defined in claim 19 wherein the communication mechanism is communicably coupled to a networked environment and transfers the vital sign parameters for analysis.

21. The mobile device defined in claim 20 wherein the networked environment comprises the internet.

* * * * *